US012685479B1

(12) United States Patent
Franklin et al.

(10) Patent No.: US 12,685,479 B1
(45) Date of Patent: Jul. 21, 2026

(54) SYSTEM FOR DIAGNOSING BARRETT'S ESOPHAGUS AND RELATED METHODS

(71) Applicant: ErasmAI LLC, Orlando, FL (US)

(72) Inventors: Daniel L. Franklin, Silver Plume, CO (US); Domenico Coppola, Orlando, FL (US); Anthony M. Magliocco, Orlando, FL (US)

(73) Assignee: ERASMAI LLC, Orlando, FL (US)

( * ) Notice: Subject to any disclaimer, the term of this patent is extended or adjusted under 35 U.S.C. 154(b) by 233 days.

(21) Appl. No.: 18/471,745

(22) Filed: Sep. 21, 2023

Related U.S. Application Data

(60) Provisional application No. 63/376,525, filed on Sep. 21, 2022.

(51) Int. Cl.

| | |
|---|---|
| *G06K 9/00* | (2022.01) |
| *A61B 5/00* | (2006.01) |
| *G06T 7/00* | (2017.01) |
| *G06V 10/26* | (2022.01) |
| *G06V 10/44* | (2022.01) |
| *G06V 10/762* | (2022.01) |
| *G06V 10/82* | (2022.01) |
| *G06V 20/69* | (2022.01) |

(52) U.S. Cl.
CPC .......... *A61B 5/4233* (2013.01); *G06T 7/0012* (2013.01); *G06V 10/273* (2022.01); *G06V 10/454* (2022.01); *G06V 10/762* (2022.01); *G06V 10/82* (2022.01); *G06V 20/695* (2022.01); *G06V 20/698* (2022.01); *G06T 2207/10056* (2013.01); *G06T 2207/20076* (2013.01); *G06T 2207/20084* (2013.01); *G06T 2207/30024* (2013.01); *G06T 2207/30092* (2013.01); *G06V 2201/03* (2022.01)

(58) Field of Classification Search
None
See application file for complete search history.

(56) References Cited

U.S. PATENT DOCUMENTS

2022/0309653 A1* 9/2022 Hassanpour ........... G06V 10/82

OTHER PUBLICATIONS

Wang et al., "Efficient and highly accurate diagnosis of malignant hematological diseases based on whole-slide images using deep learning", Jun. 2022 (Year: 2022).*

(Continued)

*Primary Examiner* — SJ Park
(74) *Attorney, Agent, or Firm* — Allen, Dyer, Doppelt + Gilchrist, PA

(57) ABSTRACT

A system is for diagnosing BE in a patient. The system includes a processor and memory, and the processor is configured to receive a WSI from an esophagus sample from the patient. The processor is configured to segment the WSI into image segments, extract features from each image segment using a CNN, and assign each image segment an attention score based upon the features. The processor is also configured to filter the image segments based upon the attention score of each image segment, and generate a BE metric value for the patient based upon the filtered image segments. The BE metric value indicates a probability that tissue with a propensity to progress to BE exists within the WSI.

20 Claims, 17 Drawing Sheets

(56) References Cited

OTHER PUBLICATIONS

Sali et al., "Deep learning for whole-slide tissue histopathology classification: A comparative study in the identification of dysplastic and non-dysplastic Barrett's esophagus", 2020 (Year: 2020).*

Lu et al. "Data-efficient and weakly supervised computational pathology on whole-slide images" Nature biomedical engineering, 5(6), 2021; 555-570.

Tan et al. "EfficientNet: Rethinking model scaling for convolutional neural networks" Proceedings of the 36th International Conference on Machine Learning, ICML 2019, Long Beach, Jun. 9-15, 2019, 6105-6114. http://proceedings.mlr.press/v97/tan19a.html Abstract Only.

Deng et al. "ImageNet: A large-scale hierarchical image database", 2009 IEEE conference on computer vision and pattern recognition: Jun. 2009; pp. 8.

Gal et al. "Dropout as a Bayesian approximation: Representing model uncertainty in deep learning" In international conference on machine learning: Jun. 2016 Abstract Only.

CLAM "Data-efficient and weakly supervised computational pathology on whole slide images—Nature Biomedical Engineering" GitHub—mahmoodlab/CLAM: Data-efficient and weakly supervised computational pathology on whole slide images—Nature BioM . . . retrieved from internet Jul. 19, 2023; pp. 15.

* cited by examiner

1100

1101

1110

1120

-BEN

-BEP

1130

1150

1160

1170

1180

1190

1200

1240

2300

SYSTEM FOR DIAGNOSING BARRETT'S ESOPHAGUS AND RELATED METHODS

RELATED APPLICATION

This application is based upon prior filed copending Application No. 63/376,525 filed Sep. 21, 2022, the entire subject matter of which is incorporated herein by reference in its entirety.

TECHNICAL FIELD

The present disclosure relates to the field of medical devices, and, more particularly, to a system for diagnosing disease and related methods.

BACKGROUND

Barrett's esophagus (BE) is a disease characterized by dysplastic progression of the esophagus lining. BE has been known to progress to esophageal adenocarcinoma in some cases, but the vast majority of patients will not end up progressing. Currently, progression is mostly monitored by surgically removing tissue, staining, mounting to a slide and having a pathologist examine the tissue characteristics to determine if cancer is present. In order to best treat the small fraction of patients that will progress, every patient needs to be monitored frequently.

SUMMARY

Generally speaking, a system is for diagnosing BE in a patient. The system comprises a processor and memory coupled thereto. The processor is configured to receive a whole slide image (WSI) from an esophagus sample from the patient. The processor is configured to segment the WSI into a plurality of image segments, extract a plurality of features from each image segment using a convolutional neural network (CNN), and assign each image segment an attention score based upon the plurality of features. The processor is also configured to filter the plurality of image segments based upon the attention score of each image segment, and generate at least one BE metric value for the patient based upon the filtered image segments, the at least one BE metric value indicating a probability that tissue with a propensity to progress to BE exists within the WSI.

In particular, the assigning may comprise ingesting the plurality of features for each image segment into an attention network. The assigning may comprise generating a plurality of branches, each branch associated with a respective class. The at least one branch may be associated with a slide-level ground truth label class.

In some embodiments, the filtering may comprise ingesting the plurality of features for each image segment into a cluster network, clustering the plurality of image segments with attention scores numerically adjacent first and second thresholds, and removing a portion of the image segments with attention scores between the first and second thresholds. The filtering may comprise removing image segments having less than a threshold amount of tissue.

Also, the at least one BE metric value may comprise a plurality thereof, the plurality of BE metric values comprising a first BE metric indicating a probability that tissue with a propensity to progress to BE exists within the WSI. The processor may be configured to directly ingest the plurality of image segments into the CNN. The extracting may comprise placing the plurality of features from each image segment in a data space less than a data space of the WSI.

Another aspect is directed to a method for diagnosing BE in a patient. The method comprises receiving a WSI from an esophagus sample from the patient, segmenting the WSI into a plurality of image segments, and extracting a plurality of features from each image segment using a CNN. The method also includes assigning each image segment an attention score based upon the plurality of features, filtering the plurality of image segments based upon the attention score of each image segment, and generating at least one BE metric value for the patient based upon the filtered image segments. The at least one BE metric value indicates a probability that tissue with a propensity to progress to BE exists within the WSI.

DETAILED DESCRIPTION

Figure 1:
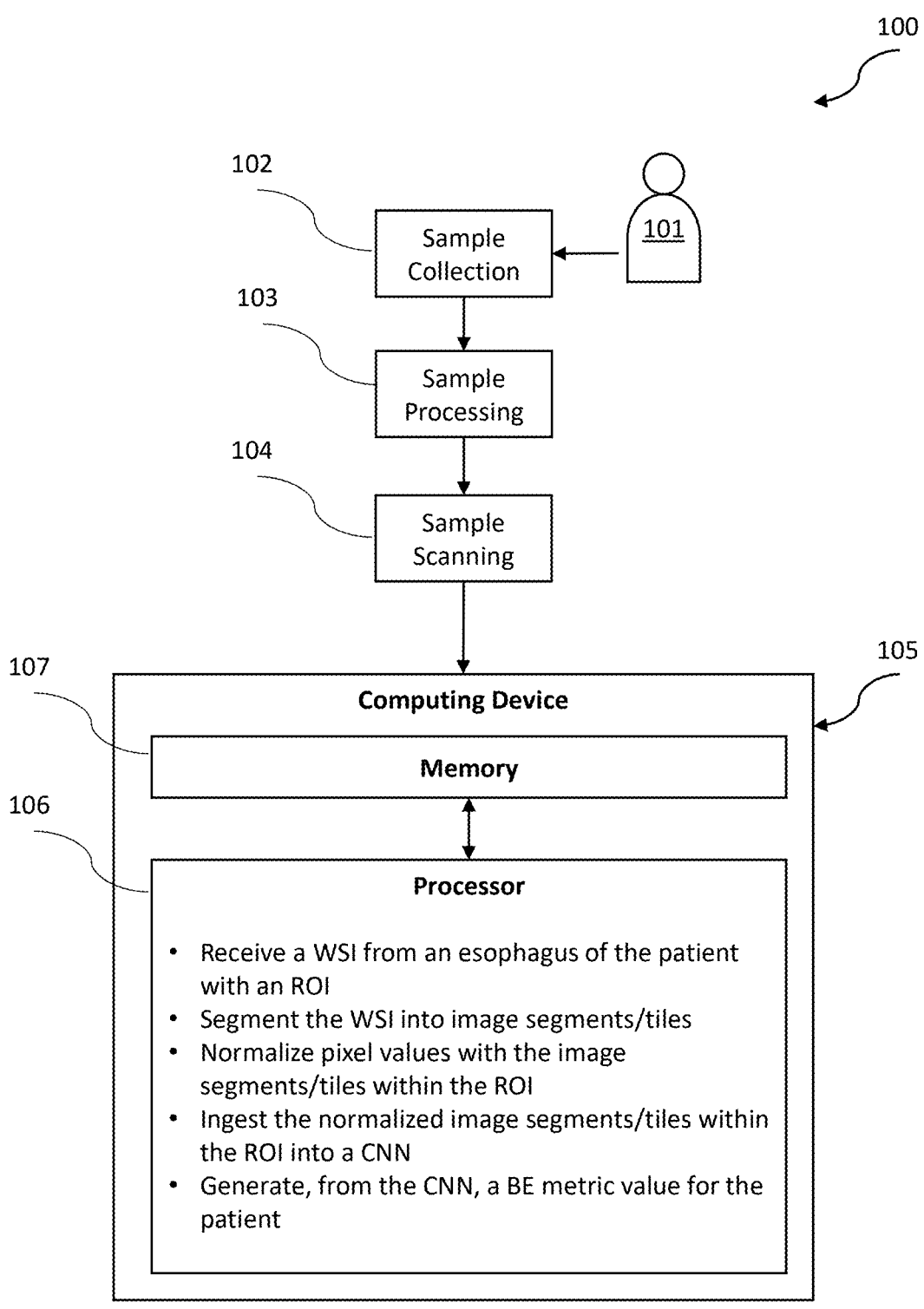
FIG. 1 is a schematic diagram of a system for diagnosing BE, according to a first embodiment of the present disclosure.

The present disclosure will now be described more fully hereinafter with reference to the accompanying drawings, in which several embodiments of the invention are shown. This present disclosure may, however, be embodied in many different forms and should not be construed as limited to the embodiments set forth herein. Rather, these embodiments are provided so that this disclosure will be thorough and complete, and will fully convey the scope of the present disclosure to those skilled in the art. Like numbers refer to like elements throughout, and base 100 reference numerals are used to indicate similar elements in alternative embodiments.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

As noted above, patients at risk for BE must be monitored rigorously. This may be inconvenient for the patient, and this approach may lead to more costly medical treatment. The present disclosure provides an approach to this problem by providing a numerical metric for the patient's risk of developing BE in the future. With the ability to accurately stratify patients, the patients who have a high risk of progressing can be more strictly monitored than typical patients. The following disclosure is directed to the systems and methods which are in place to process an image of hematoxylin- and eosin-stained esophagus tissue and determine progression status.

Referring initially to FIG. 1, a system 100 according to the present invention is now described. The system 100 is for diagnosing BE in a patient 101. The system 100 illustratively comprises a sample collection module 102. As will be appreciated, the sample collection module 102 comprises collecting a tissue sample from an esophagus of the patient 101. The system 100 illustratively comprises a sample processing module 103 downstream from the sample collection module 102. The sample processing module 103 comprises mounting the tissue sample to a substrate/slide (e.g., glass or polymer plate), and staining the mounted tissue sample for enhancing visibility of characteristic within the tissue sample. The staining of the mounted tissue sample may comprise a hematoxylin and eosin stain, or a lymphocyte stain, for example.

The system 100 illustratively comprises a sample scanning module 104 downstream from the sample processing module 103. The sample scanning module 104 comprises scanning the stained mounted tissue sample to generate a digital image. As will be appreciated, the digital image may comprise a WSI file, for example, using the following file formats: Aperio (.sys, .tif); Hamamatsu (.vms, .vmu, .ndpi); Leica (.scn); MIRAX (.mrxs); Philips (.tiff); Sakura (.svslide); Trestle (.tif); Ventana (.bif, .tif); and Generic tiled TIFF (.tif).

The system 100 illustratively comprises computing device 105 comprising a processor 106 and memory 107 coupled thereto. The processor 106 cooperates with the memory 107 to perform operations detailed herein. It should be appreciated the computing device 105 may comprise a standalone computing device, or may be provided as assigned resources within a cloud computing platform (CCP), such as Amazon Web Service, Microsoft Azure, or Google Cloud Platform.

The processor 106 is configured to receive the WSI from the esophagus sample of the patient with a ROI therein. In some embodiments, the ROI is designated out of band based upon a manual user annotation process. In particular, the user may view the WSI via a software viewer (e.g., Proscia or UPath) and then annotate the ROI. For example, the user may view the WSI via a typical WSI viewer software and encircle areas (i.e., areas with biological features of interest, such as metaplasia) to be designated as within the ROI. In other embodiments, the processor 106 is configured to designate the ROI without user input based upon image processing techniques, such as a change detection process, or a visual filtering process. In some embodiments, the processor 106 may be configured to ingest a plurality of WSIs from the patient 101, for example, using varying staining techniques.

The processor 106 is configured to segment the WSI into a plurality of image segments (or image tiles) (e.g., using slide manipulation software, such as OpenSlide). For example, each image segment may comprise a rectangle-shaped segment, each side of the rectangle shaped segment having a pixel length of about 1000 (i.e., ±25% of 1000, e.g., 512 pixel×512 pixels). Image segments having a threshold portion (e.g., between 10% and 90%) within the ROI are classified as image segments within the ROI. Also, a programming script that tiles the WSI may convert the coordinates of the ROI annotation from the software's form to a form that the tiling script is able to read. In some embodiments, the images segments may be augmented by rotating in 90° increments and mirroring for training of the model.

The processor 106 is further configured to normalize pixel values with the image segments within the ROI. The image data is divided into three channels (i.e., red, green and blue), and the pixel values correspond to the amount of light each cluster of RGB should output to properly mix into the correct color. In some embodiments, the pixel values are normalized by measuring the mean and standard deviation of every pixel for each channel. The calculated mean will be referred to as the channel mean, and the calculated standard deviation will be referred to as channel standard deviation. The pixels are then normalized by the equation:

$$\text{Normalized pixel value} = (\text{pixel value} - \text{channel mean}) / \text{channel standard deviation}.$$

During training, the pixel values for each and every image segments within the ROI are normalized. Subsequently, during the model will ingest and normalize image segments using the same process.

The processor 106 is configured to ingest the normalized image segments within the ROI into a CNN model. The CNN may be configured to extract features from the normalized image segments within the ROI and associate the features with nodes within a neural network. In particular, the generation of the CNN, according to an example embodiment, is detailed herein. For example, a Pytorch (open source project available on GitHub) dataloader is an iterable object that provides batches of inputs for the model to act upon. The model itself is a CNN also made from PyTorch functions.

As will be appreciated, the CNN uses filters to extract features from images and connect the collections of features to a predictive probability distribution through layers of nodes connected through linear regression. The nodes are just placeholders for numbers and the connection signifies that the value in a node is determined by the output of the equation (linear regression) given the value in the connected input node. For example, the CNN may comprise an EfficientNet type CNN. (See Tan et al., 2019, May, "EfficientNet: Rethinking model scaling for convolutional neural networks", International conference on machine learning, pages 6105-6114). The EfficientNet CNN is also open sourced and available on GitHub. The basic architecture or connection of nodes is what is open sourced, sometimes along with some trained parameters from common benchmark datasets, for example, ImageNet (as disclosed in Deng, J. et al., 2009, June, "ImageNet: A large-scale hierarchical image database", 2009 IEEE conference on computer vision and pattern recognition, pages 248-255, IEEE), the entire contents of which are hereby incorporated by reference.

Further, the processor 106 is configured to send the extracted features to a fully connected section, which is most simply described as comprising layers connected by linear regression, but can also include drop out layers, batch normalization, and other layer types. The CNNs are able to take in as input an image and output a probability distribution of which classes exist within the image. The CNN is a feature extractor and classifier put together. In the CNN, the feature extractor applies filters to the image to produce a collection of feature maps, and the classifier takes as input the collection of feature maps and outputs a probability distribution of which classes exist within the image.

The machine learning model may use this basic architecture, initialize the adjustable parameters either randomly or from another model trained on another dataset, and update the parameters to best perform on the new dataset. This dataset was developed by taking slides of BE and identifying whether they have progressed within the last 10 years or not. This created two groups, BE negative (BEN) and BE positive (BEP). The tiles within the slides were given the same label (BEN or BEP) as the slide. Only areas with goblet cells (which are cells known to occur in areas affected by BE) were used to develop the model. The dataset is separated into three partitions: a training, a validation, and a test. The validation partition is used to determine when to stop training and the test partition is used to determine the performance of the model. During training, after the parameters have been updated to fit each image in the dataset to the closest output to what is expected, the performance is measured on the validation set. Once the performance has stopped increasing after a few rounds of training, which may also be referred to as an epoch, training stops and statistics are measured on the predictions of the resulting model on the test set.

The processor 106 is configured to generate, from the CNN, a plurality of BE metric values for the patient 101. The plurality of BE metric values indicates a probability that tissue with a propensity to progress to BE exists within the WSI. In some embodiments, the plurality of BE metric values may comprise a first BE metric indicating a probability of the patient 101 developing BE in three years, a second BE metric indicating a probability that tissue with a propensity to progress to BE exists within the WSI in five years, and a third BE metric indicating a probability that tissue with a propensity to progress to BE exists within the WSI in ten years.

In particular, the output of the model may comprise a predictive probability distribution. It has been shown that Monte Carlo simulations can be performed with a slight modification to the model and may be able to measure model predictive confidence, which may also be referred to as uncertainty. A Monte Carlo simulation estimates an unknown number by using random sampling. A well-known example is the estimation of an area of a circle within a square of known dimensions. Since the area of the square is known, the ratio between the area of the square and area of the circle can allow estimation of the area of the circle. The ratio between random points selected within the square to points within the circle should approach the ratio of the two areas as more points are drawn. Using a dropout layer during inference is analogous to this, shown to measure the uncertainty of the model. (See Gal et al., 2016, June, "Dropout as a Bayesian approximation: Representing model uncertainty in deep learning. In international conference on machine learning", pages 1050-1059, PMLR). The dropout layer randomly omits the connection between nodes and is used during training to allow parameters to be less reliant on each other and increase model robustness. If used during inference the model will have slightly different outputs each time and the variance in these outputs (measured by standard deviation or entropy, etc.) is considered model uncertainty.

Measuring uncertainty in a model is a step in creating a safe product, and this assures that inputs for which the model was not trained on are able to be passed onto a human decision maker to avoid an uncertain, incorrect prediction. For a model to predict with certain features, they need to be present in the training dataset. It can never be certain that a given training set contains all of the necessary features to make informed predictions on every patient it will predict on, so measuring model uncertainty allows for the model to omit making a prediction in cases where there are features present that the model hasn't been trained on.

Another way to probe how the model is making a prediction is through Grad-CAM++. Grad-CAM is a generalization of class activation mapping (CAM), an older technique, and doesn't require adjusting the architecture of the network like CAM does. With Grad-CAM, the gradient values are measured with respect to the feature maps in the last convolutional layer since this layer should respond to the most complex features which are made up of other features. The gradients are global average pooled (i.e., the average of all values within a feature map sized gradient matrix). Grad-CAM is the result of a combination of these feature maps superimposed on the image and weighted with the global average pooled result after being input into a rectified linear unit equation in addition to other pixel space gradient visualization techniques such as guided backpropagation and deconvolution. Grad-CAM++ is a generalization of Grad-CAM and introduces a pixel wise weighting of the gradients with respect to a particular spatial position in the feature map of the last layer rather than weighting the feature map by size. In some embodiments, the model may be configured to be gender specific.

Figure 2:
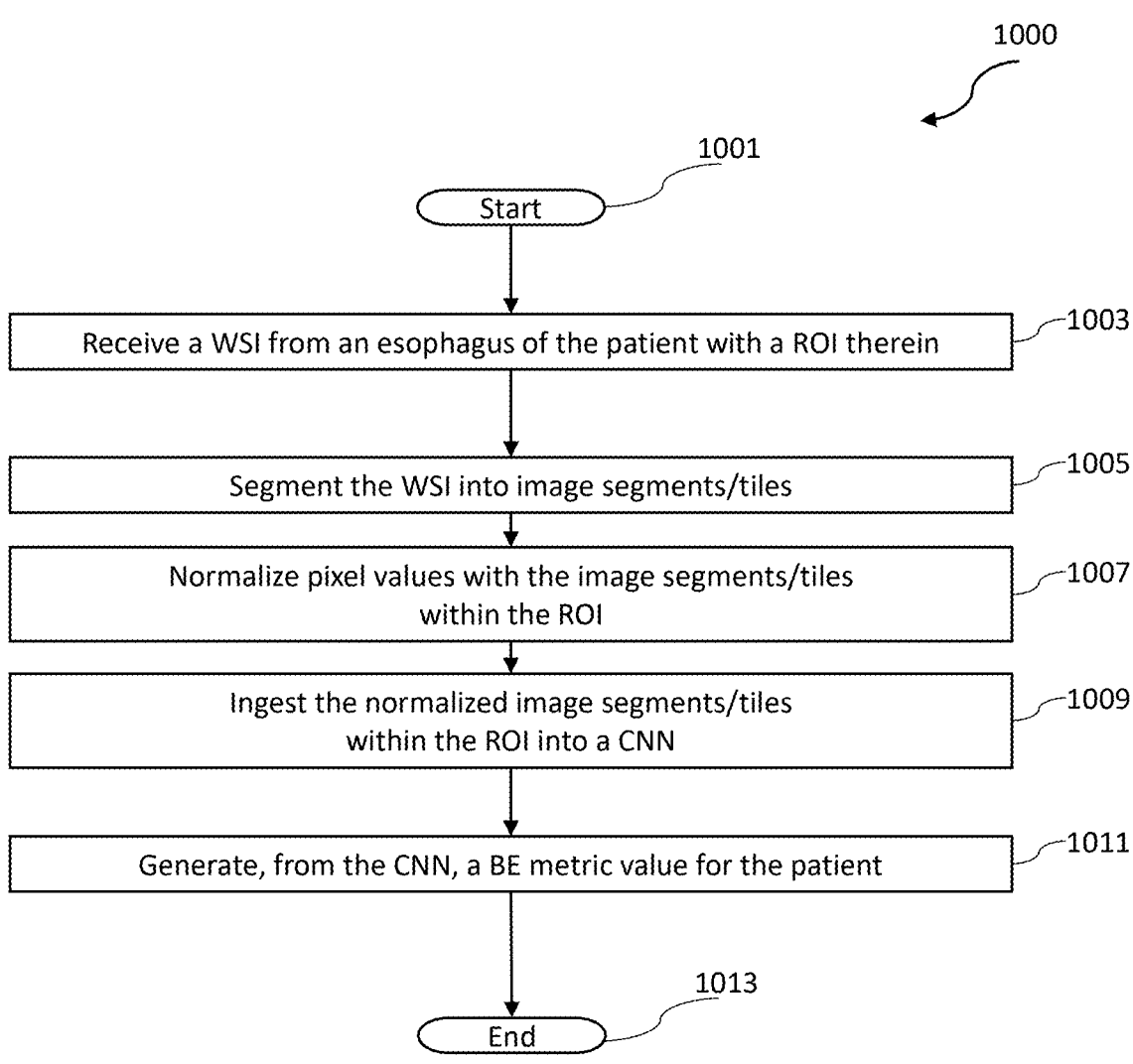
FIG. 2 is a flowchart illustrating a method for diagnosing BE, according to the first embodiment of the present disclosure.
Figure 3A:
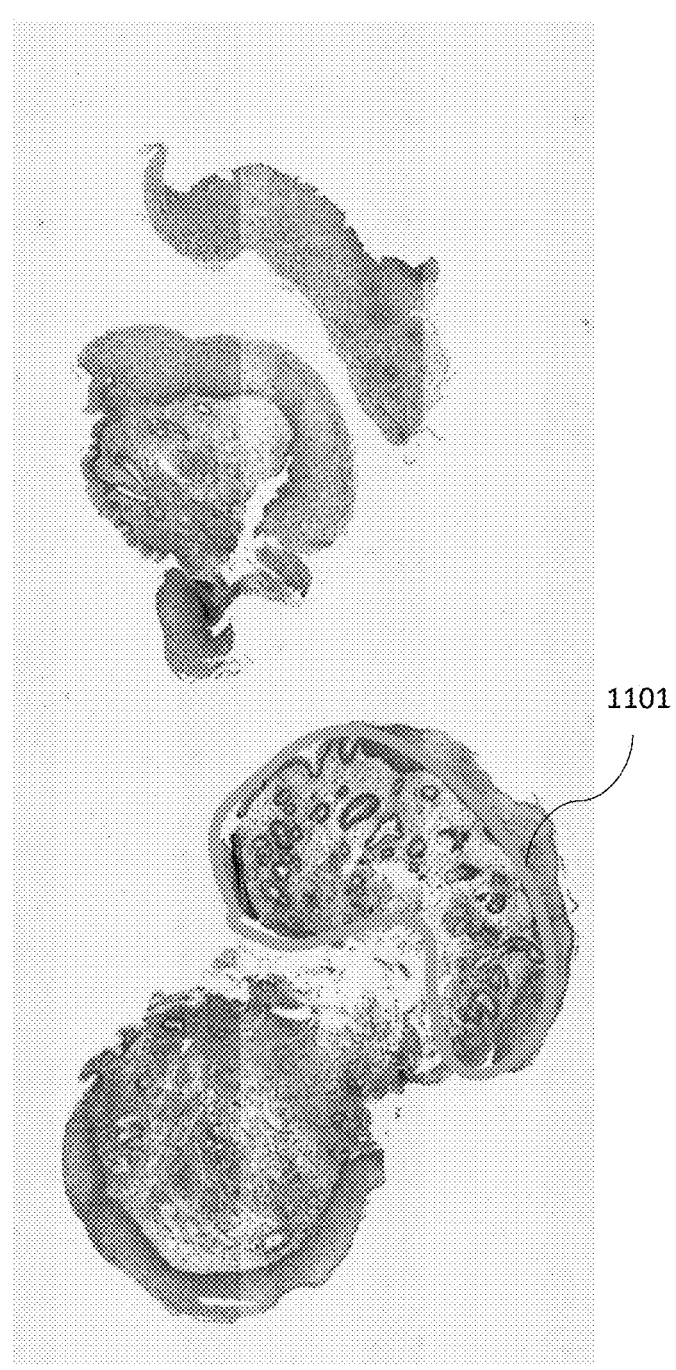
FIGS. 3A-3D are images of a WSI during processing in the system of FIG. 1.
Figure 3B:
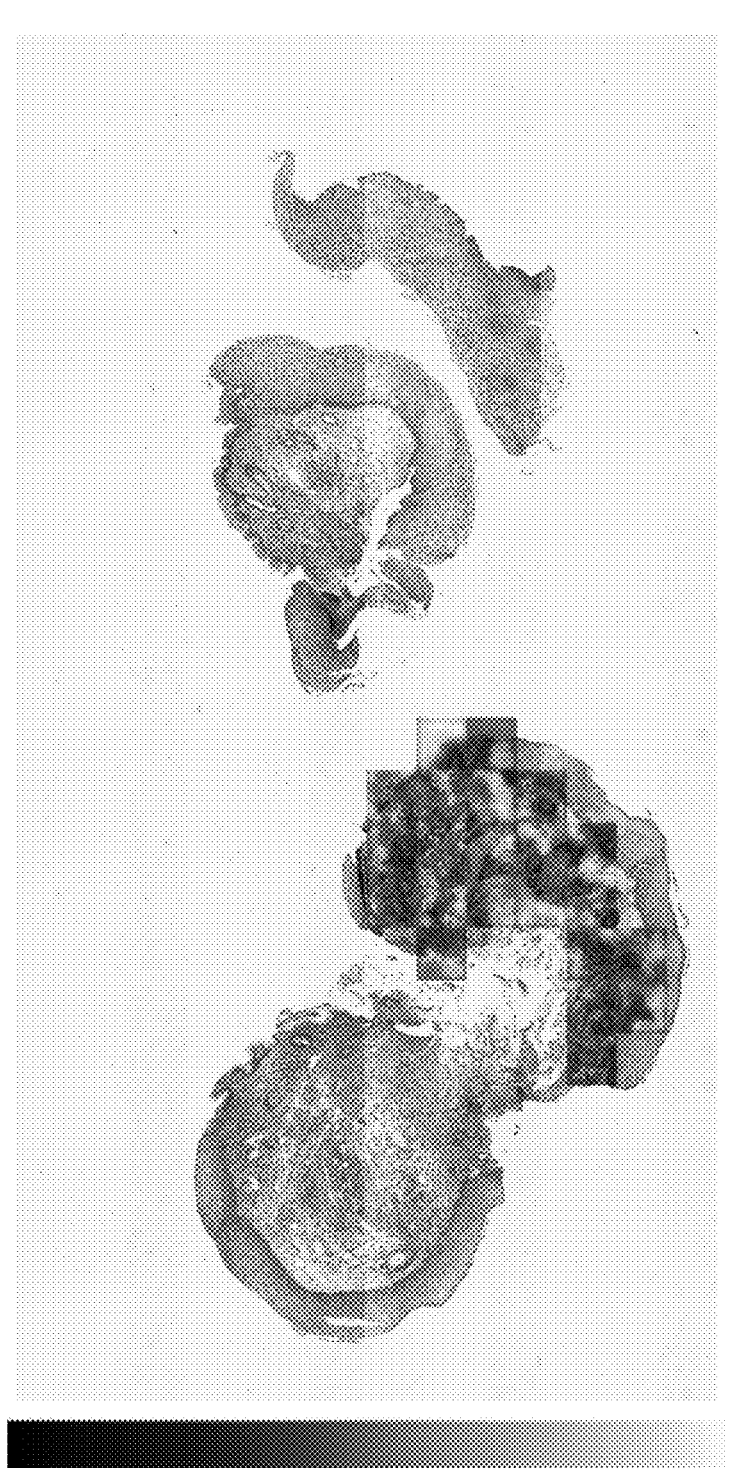
Figure 3C:
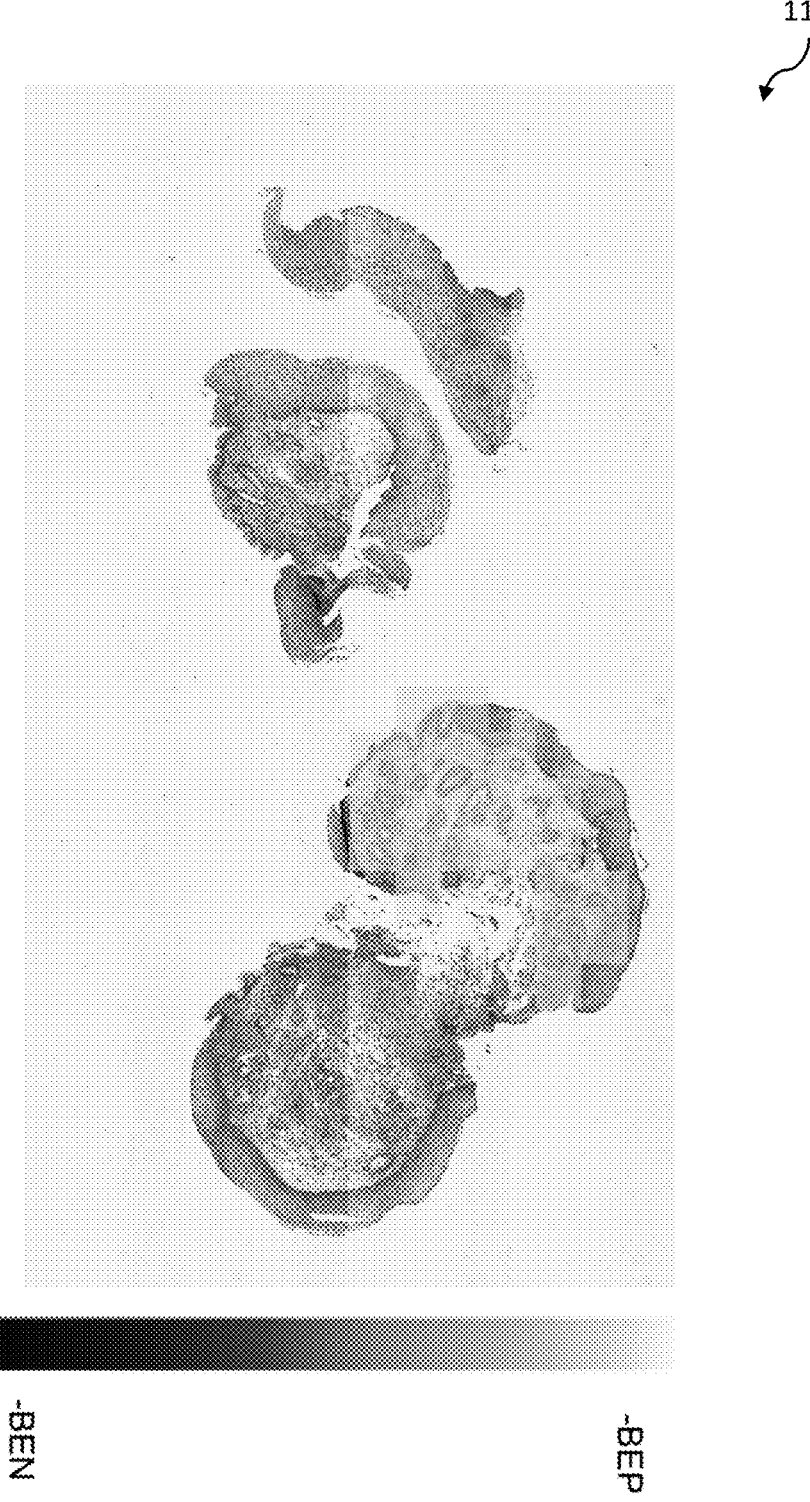
Figure 3D:
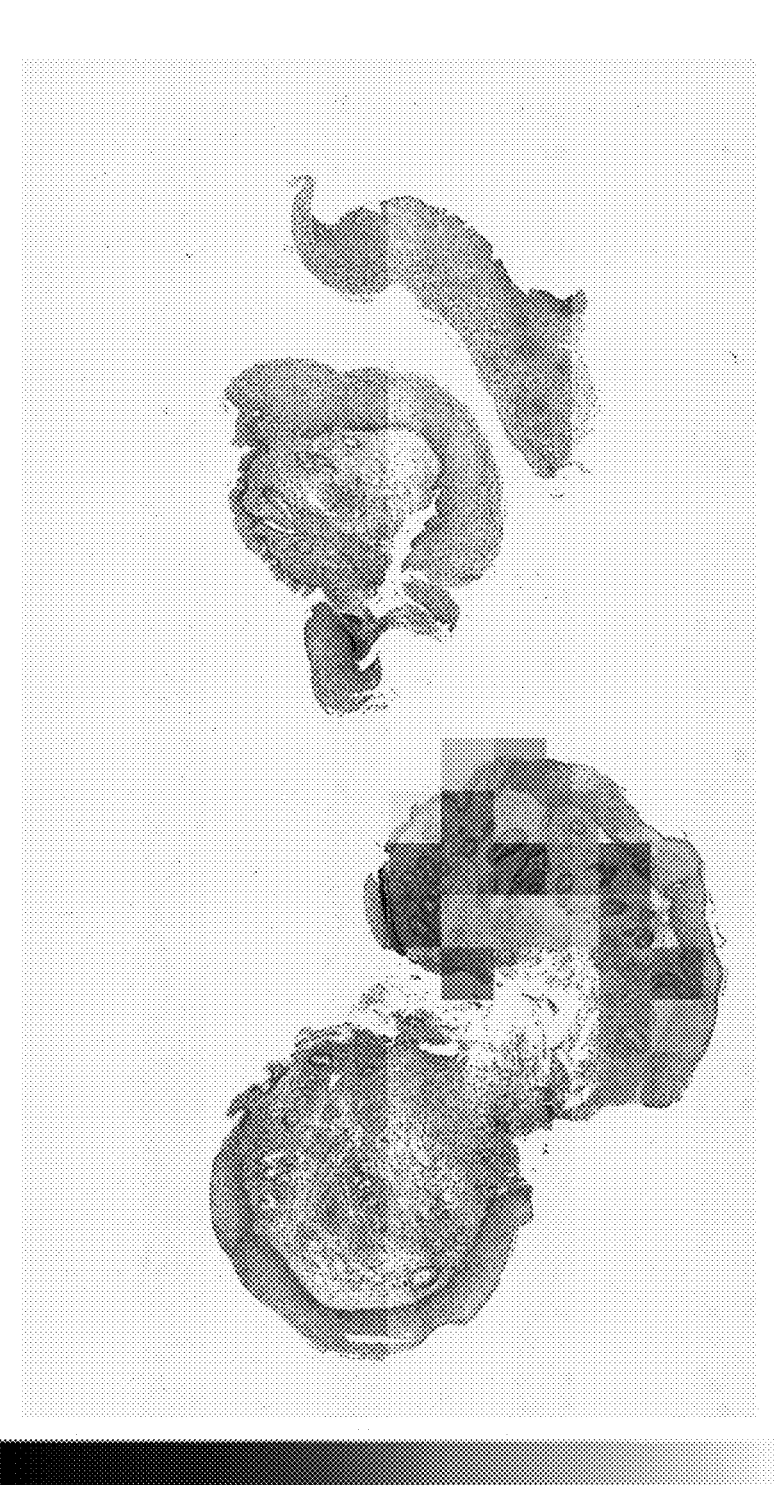
Figures 4A, 4B:
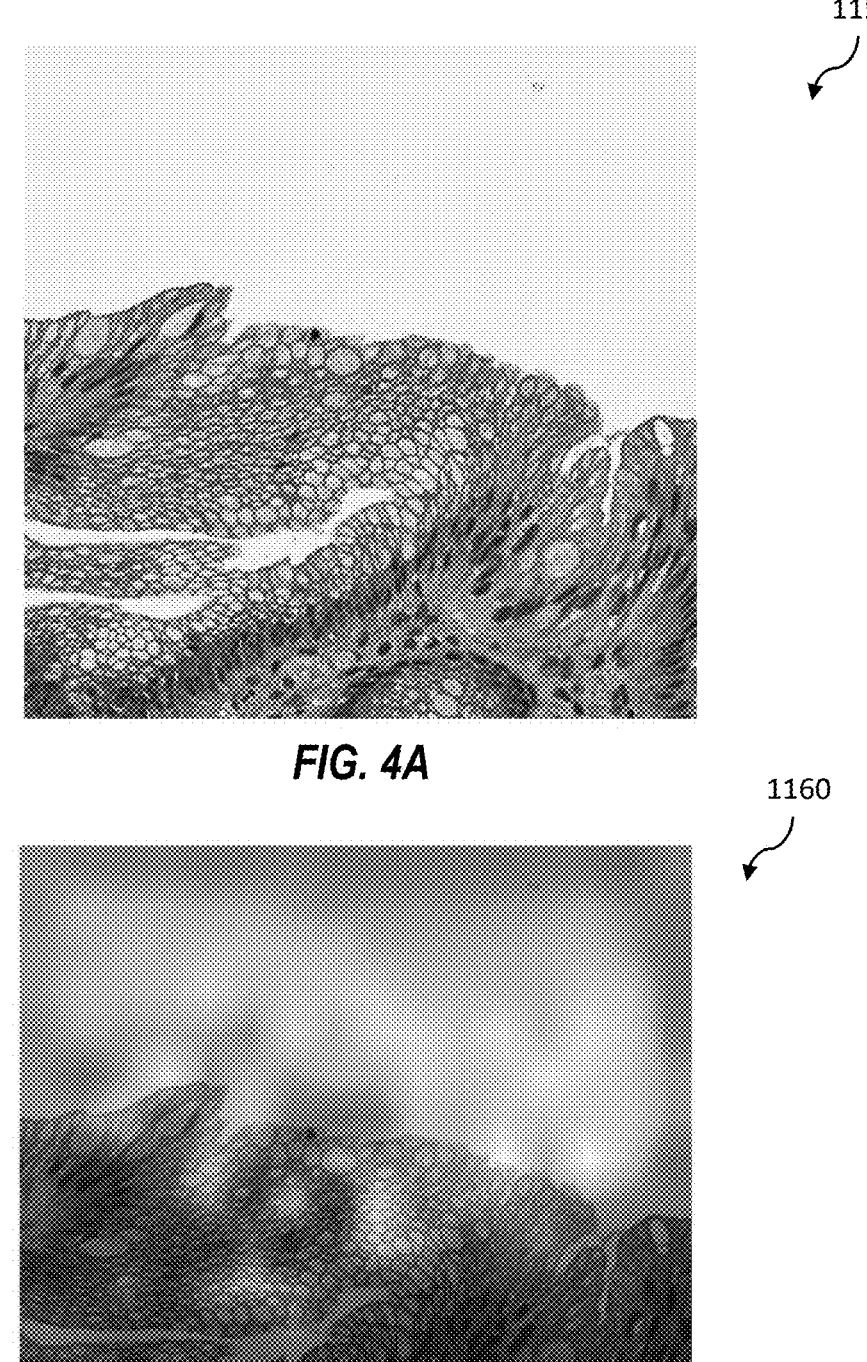
FIGS. 4A-4B are diagrams of a WSI before processing and subsequent to processing, respectively.
Figures 5A, 5B:
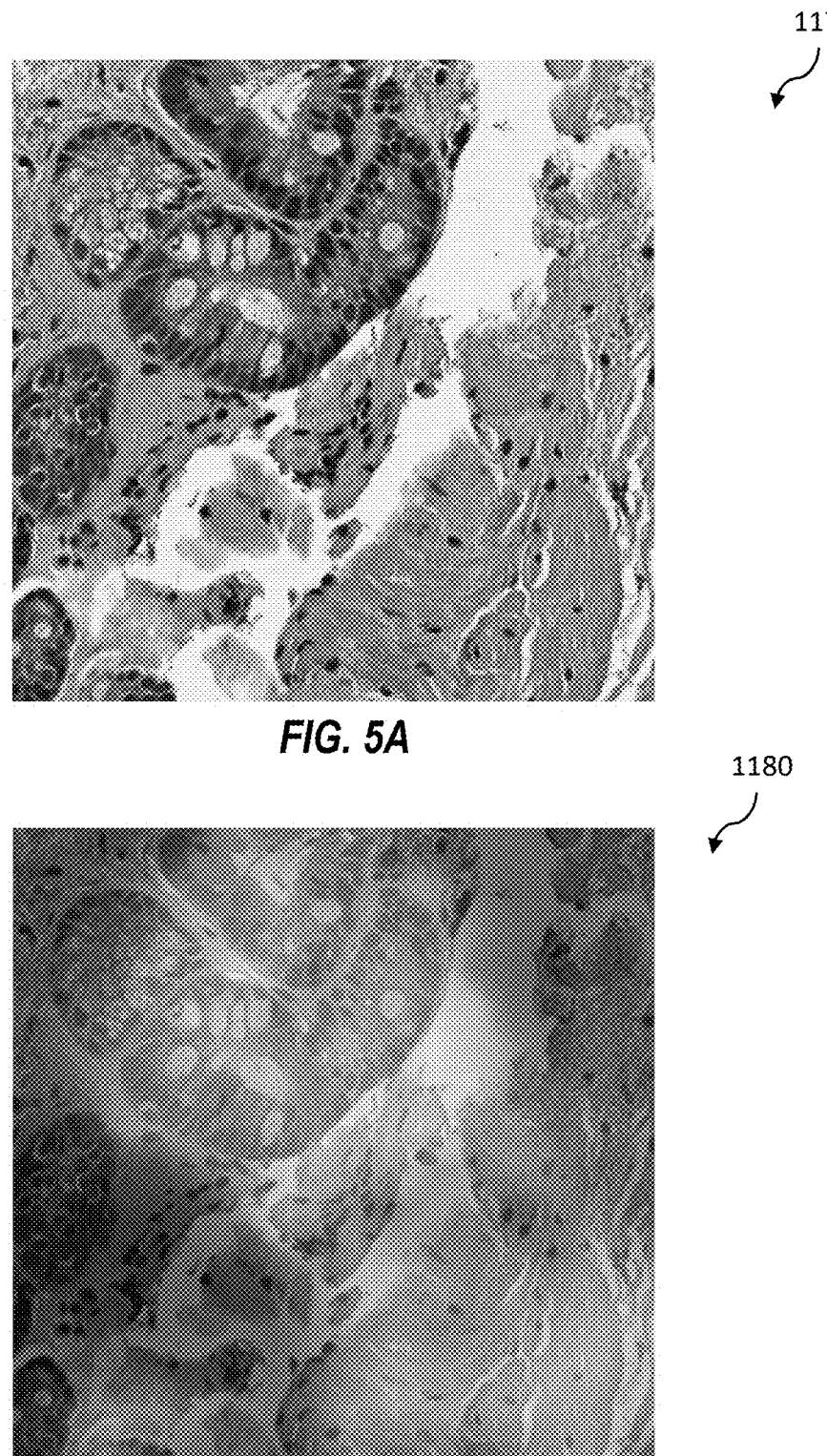
FIGS. 5A-5B are diagrams of a WSI before processing and subsequent to processing, respectively.
Figure 6A:
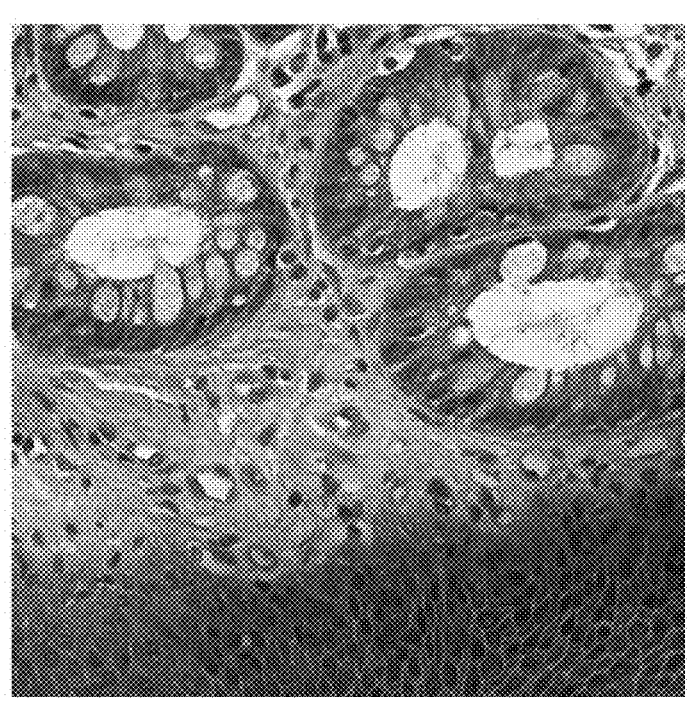
FIGS. 6A-6B are diagrams of a WSI before processing and subsequent to processing, respectively.
Figure 6B:
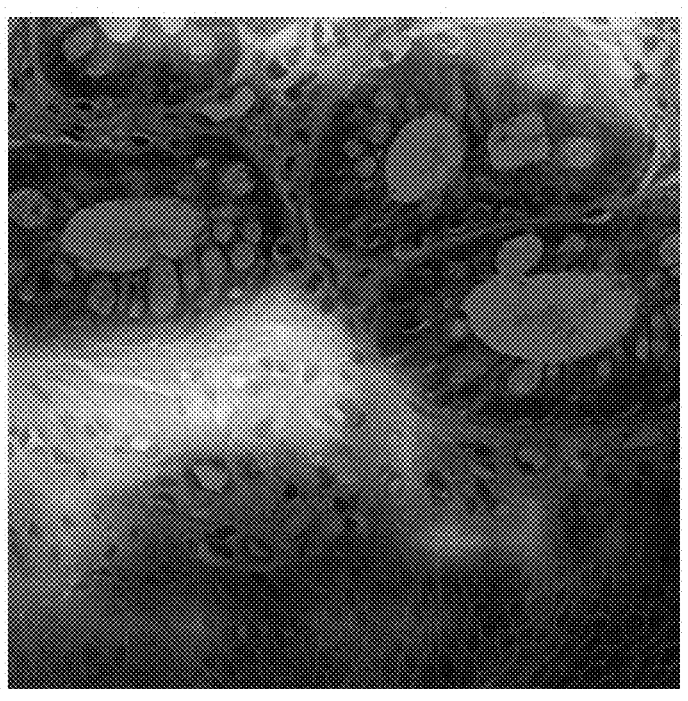
Figure 7A:
FIGS. 7A-7B are diagrams of a WSI before processing and subsequent to processing, respectively.
Figure 7A:
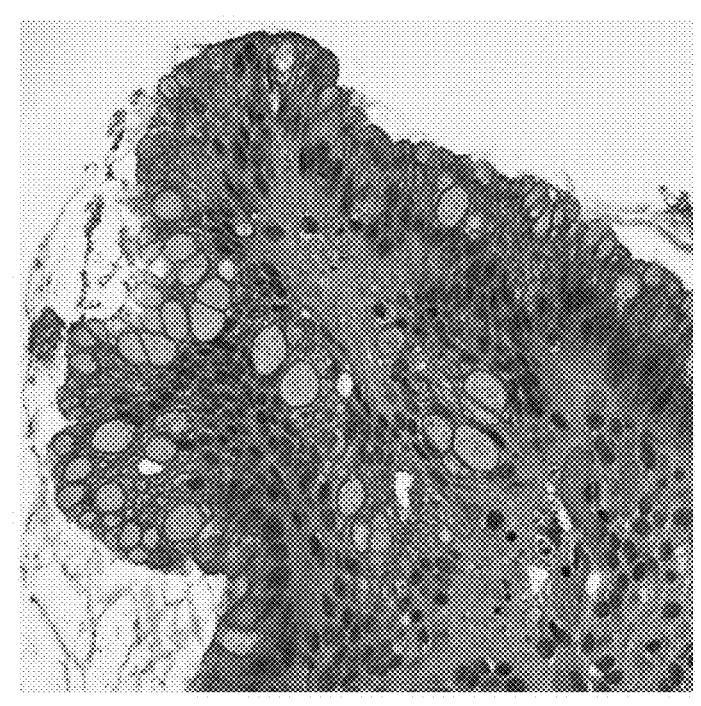
Figure 7B:
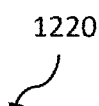
Figure 7B:
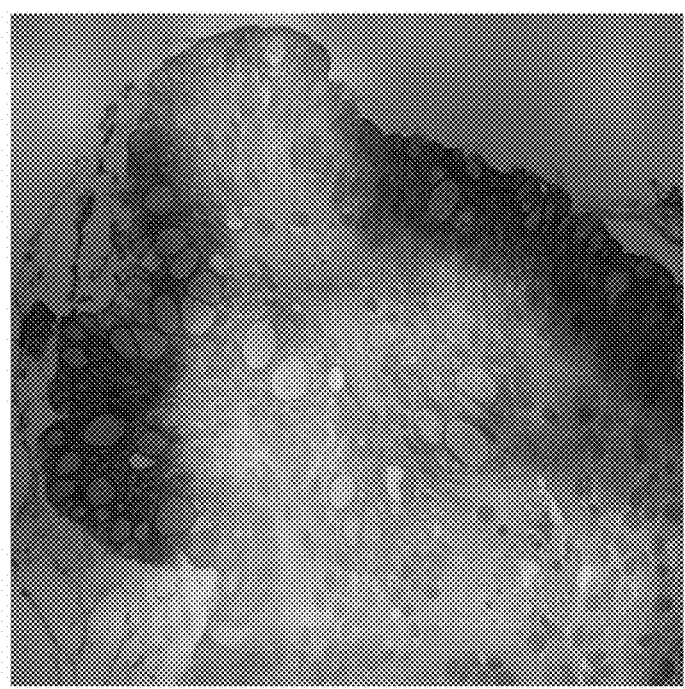

Referring now additionally to FIG. 2 and a flowchart 1000 therein, a method for diagnosing BE in a patient 101 is now described, which begins at Block 1001. The method comprises receiving a WSI from an esophagus sample of the patient with a ROI therein, and segmenting the WSI into a plurality of image segments. (Blocks 1003, 1005). The method comprises normalizing pixel values with the image segments within the ROI, ingesting the normalized image segments within the ROI into a convolutional neural network (CNN), and generate, from the CNN, at least one BE metric value for the patient, the at least one BE metric value indicating a probability that tissue with a propensity to progress to BE exists within the WSI. (Blocks 1007, 1009, 1011). The method ends at Block 1013.

Referring now to FIGS. 3A-3D, diagrams 1100, 1110, 1120, 1130 show a WSI during processing by an example embodiment of the CNN disclosed herein. Diagram 1100 shows the WSI with the annotated ROI 1101. Diagram 1110 shows the WSI with a Grad-CAM++ visualization. Diagram 1120 shows the WSI with a prediction visualization. Diagram 1130 shows the WSI with an uncertainty (Monte Carlo) visualization.

Referring now to FIGS. 4A-7B, diagrams 1150, 1160, 1170, 1180, 1190, 1200, 1210, 1220 show a WSI during processing by an example embodiment of the CNN disclosed herein. Diagram 1150 shows an image segment from the WSI, the model classifying the image segment as BE positive. Diagram 1160 shows a Grad-CAM++ processing of the image segment. This example shows the modeling making a prediction with significant whitespace, which indicates that the model is over fit to the training dataset.

Diagram 1170 shows an image segment from the WSI, the model classifying the image segment as BE positive. Diagram 1180 shows a Grad-CAM++ processing of the image segment. Diagram 1190 shows an image segment from the WSI, the model classifying the image segment as BE negative. Diagram 1200 shows a Grad-CAM++ processing of the image segment. Diagram 1210 shows an image segment from the WSI, the model classifying the image segment as BE negative. Diagram 1220 shows a Grad-CAM++ processing of the image segment.

In Table 1 below, performance metrics of the model on the test dataset (n=8,248 tiles, 6 slides) are shown. The low specificity suggests that the model needs additional samples for training.

TABLE 1

|  | Sensitivity | Specificity | AUC |
| --- | --- | --- | --- |
| Tile | 97.10% | 55.42% | 0.76 |
| Slide | 100% | 66.67% | 0.83 |

Figure 8:
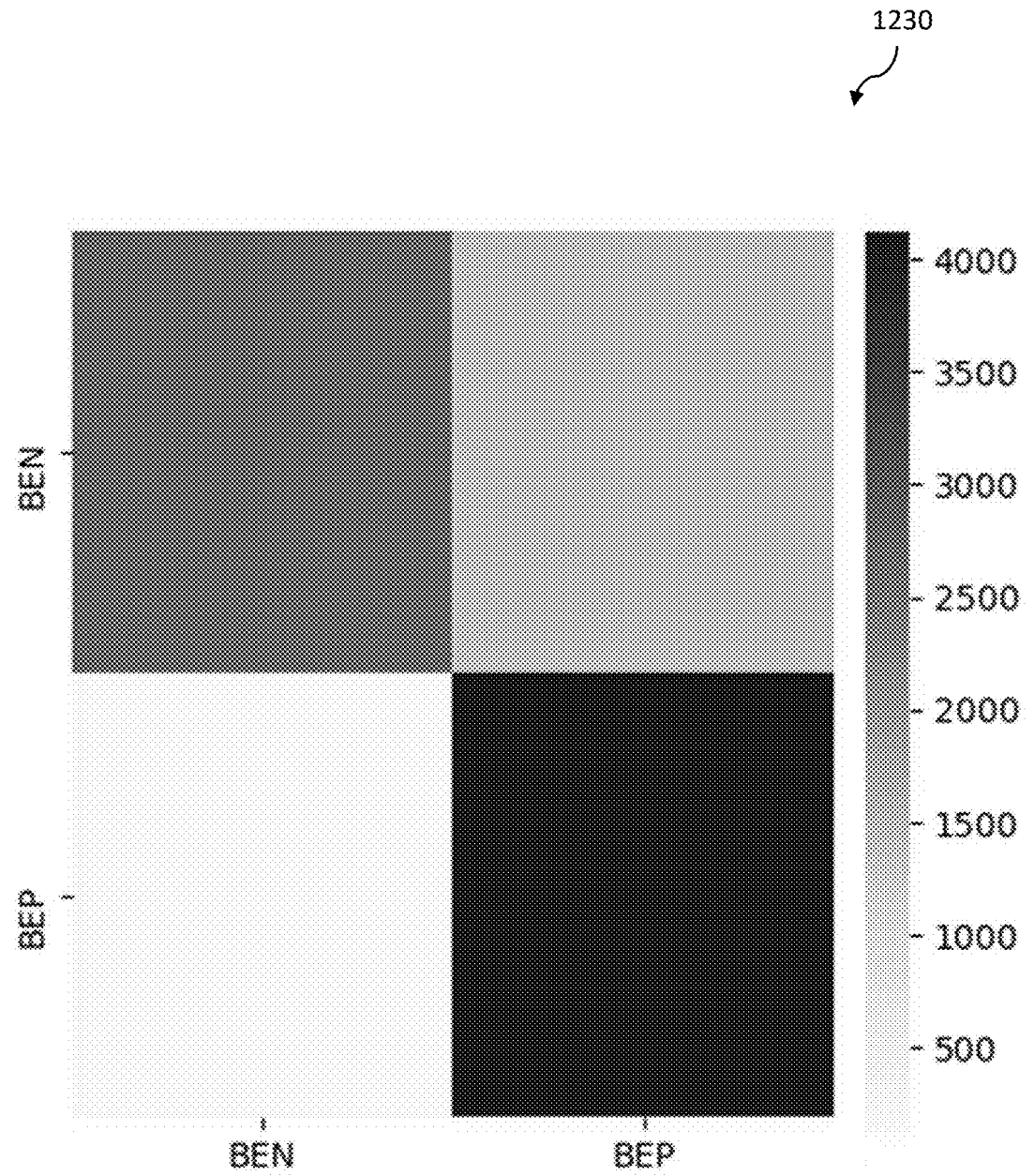
FIG. 8 is a diagram of a confusion matrix from results of a test set in the system, according to the present disclosure.
Figure 9:
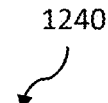
FIG. 9 is a diagram of Monte Carlo simulations for testing in the system, according to the present disclosure.
Figure 9:
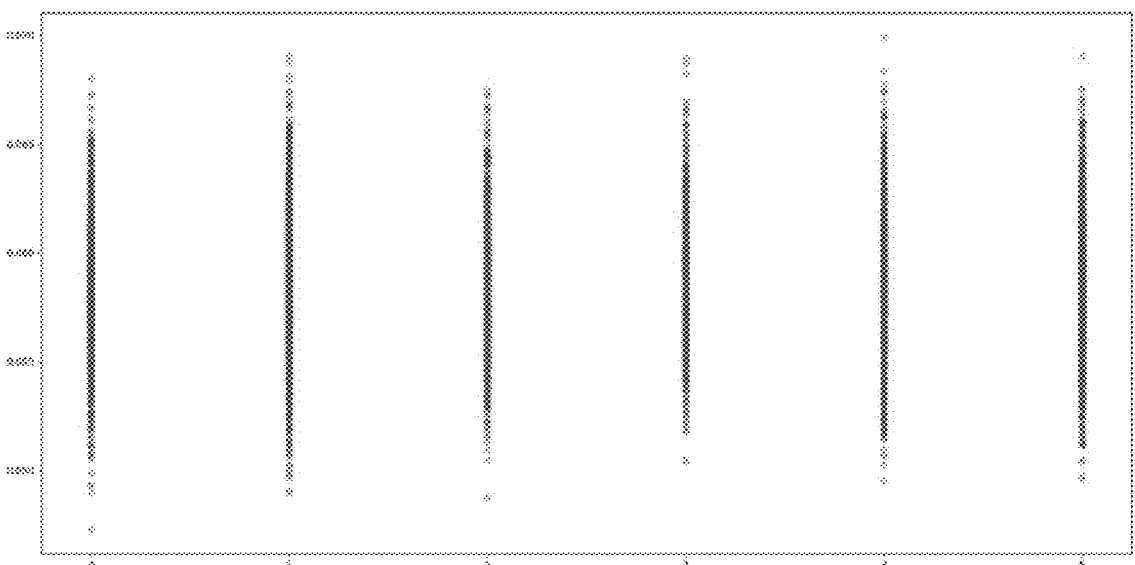

Referring now to FIGS. 8-9, the performance of the model is discussed with reference to diagrams 1230, 1240. Diagram 1230 is a confusion matrix of predictions from the test set. Diagram 1240 shows the results of the Monte Carlo simulations for each of the 6 slides in the test set. Here, 100 predictions for each tile were made, with the dropout layer activated; and the standard deviation of those 100 predictions is shown in the diagram 1240.

It should be appreciated that the disclosure is not limited to the diagnosis of BE. Indeed, the system 100 may be readily applied to diagnosis of other diseases and conditions that are typically diagnosed using manual review of patient tissue samples. The system 100 may be used to diagnose any form of dysplasia (e.g., hip dysplasia, myelodysplastic syndrome, and multicystic dysplastic kidney) in the patient 101.

Helpfully, the system 100 disclosed herein provides early notice of potential dysplasia or BE. With the early diagnosis, the intervention with the patient 101 may comprise simple removal of the effected tissue.

Generally, a system is for diagnosing BE in a patient. The system comprises a processor and memory coupled thereto. The processor is configured to receive a WSI from an esophagus sample of the patient with a ROI therein, and segment the WSI into a plurality of image segments. The processor is further configured to normalize pixel values with the image segments within the ROI, ingest the normalized image segments within the ROI into a CNN, and generate, from the CNN, at least one BE metric value for the patient. The at least one BE metric value indicates a probability of the patient developing BE.

In some embodiments, the at least one BE metric value may comprise a plurality thereof. The plurality of BE metric values may comprise a first BE metric indicating a probability that tissue with a propensity to progress to BE exists within the WSI. The CNN may be configured to extract features from the normalized image segments within the ROI and associated the features with nodes within a neural network.

Another aspect is directed to a method for diagnosing BE in a patient. The method comprises receiving a WSI from an esophagus sample of the patient with a ROI therein, and segmenting the WSI into a plurality of image segments. The method comprises normalizing pixel values with the image segments within the ROI, ingesting the normalized image segments within the ROI into a CNN, and generating, from the CNN, at least one BE metric value for the patient. The at least one BE metric value indicates a probability that tissue with a propensity to progress to BE exists within the WSI.

Referring now to FIGS. 10-14, a system 200 according to the present disclosure is now described. The system 200 is for diagnosing BE in a patient 201. The system 200 illustratively comprises a sample collection module 202. As will be appreciated, the sample collection module 202 comprises collecting a tissue sample from an esophagus of the patient 201. The system 200 illustratively comprises a sample processing module 203 downstream from the sample collection module 202. The system 200 illustratively comprises a sample scanning module 204 downstream from the sample processing module 203. The system 200 illustratively comprises computing device 205 comprising a processor 206 and memory 207 coupled thereto. The processor 206 cooperates with the memory 207 to perform operations detailed hereinbelow.

The processor 206 is configured to receive a WSI from an esophagus sample from the patient 201. As perhaps best seen in diagram 2300 of FIG. 12, the processor 206 is configured to segment the WSI into a plurality of image segments. For example, in one embodiment, each of the plurality of image segments comprise a 256 pixel×256 pixel image segment. The processor 206 is configured to extract a plurality of features from each image segment using a CNN. Because of the reduced size of the image segments, the processor 206 may be configured to directly ingest the plurality of image segments into the CNN (e.g., pretrained CNN). Also, the extracting may place the plurality of features from each image segment in a data space less than a data space of the WSI. The plurality of image segments is encoded once by the CNN into a descriptive feature representation. During training and inference, extracted patches in each WSI are passed to a model as feature vectors.

Following this feature extraction, both training and inference can occur in the low-dimensional feature space rather than the high-dimensional pixel space. The volume of the data space is decreased nearly 200-fold, and this can drastically reduce the subsequent computation required to train supervised deep learning models. Advantageously, working with a low-dimensional feature space enables training models on thousands of gigapixel-sized resection slides within hours on modern consumer-grade workstations.

The processor 206 is configured to assign each image segment an attention score based upon the plurality of features. In some embodiments and as perhaps best seen in diagram 2100 of FIG. 13, the assigning may comprise ingesting the plurality of features for each image segment into an attention network. The assigning illustratively comprises generating a plurality of branches 2101a-2101n, each branch associated with a respective class. One or more branches 2101n are associated with a slide-level ground truth label class.

For each class, the attention network ranks each region in the WSI and assigns an attention score based on its relative importance to the slide-level diagnosis. Attention-pooling weighs patches by their respective attention scores and summarizes patch-level features into slide-level representations, which are used to make the final diagnostic prediction. The strongly attended and weakly attended regions are used as representative samples to train clustering layers that learn a rich patch-level feature space separable between the positive and negative evidence of distinct classes.

The processor 206 is also configured to filter the plurality of image segments based upon the attention score of each image segment. In some embodiments and as perhaps best seen in diagram 2200 of FIG. 14, the filtering comprises ingesting the plurality of features for each image segment into a cluster network, clustering the plurality of image segments with attention scores numerically adjacent first and second thresholds, and removing a portion of the image segments with attention scores between the first and second thresholds (i.e., upper and lower thresholds). Generally, the filtering comprises removing image segments having less than a threshold amount of tissue.

The processor 206 is also configured to generate a plurality of BE metric values for the patient based upon the filtered image segments. In particular, one or more of the plurality of BE metric values indicate a probability that tissue with a propensity to progress to BE exists within the WSI. Also, the plurality of BE metric values may comprise a first BE metric indicating a probability that tissue with a propensity to progress to BE exists within the WSI.

Figure 10:
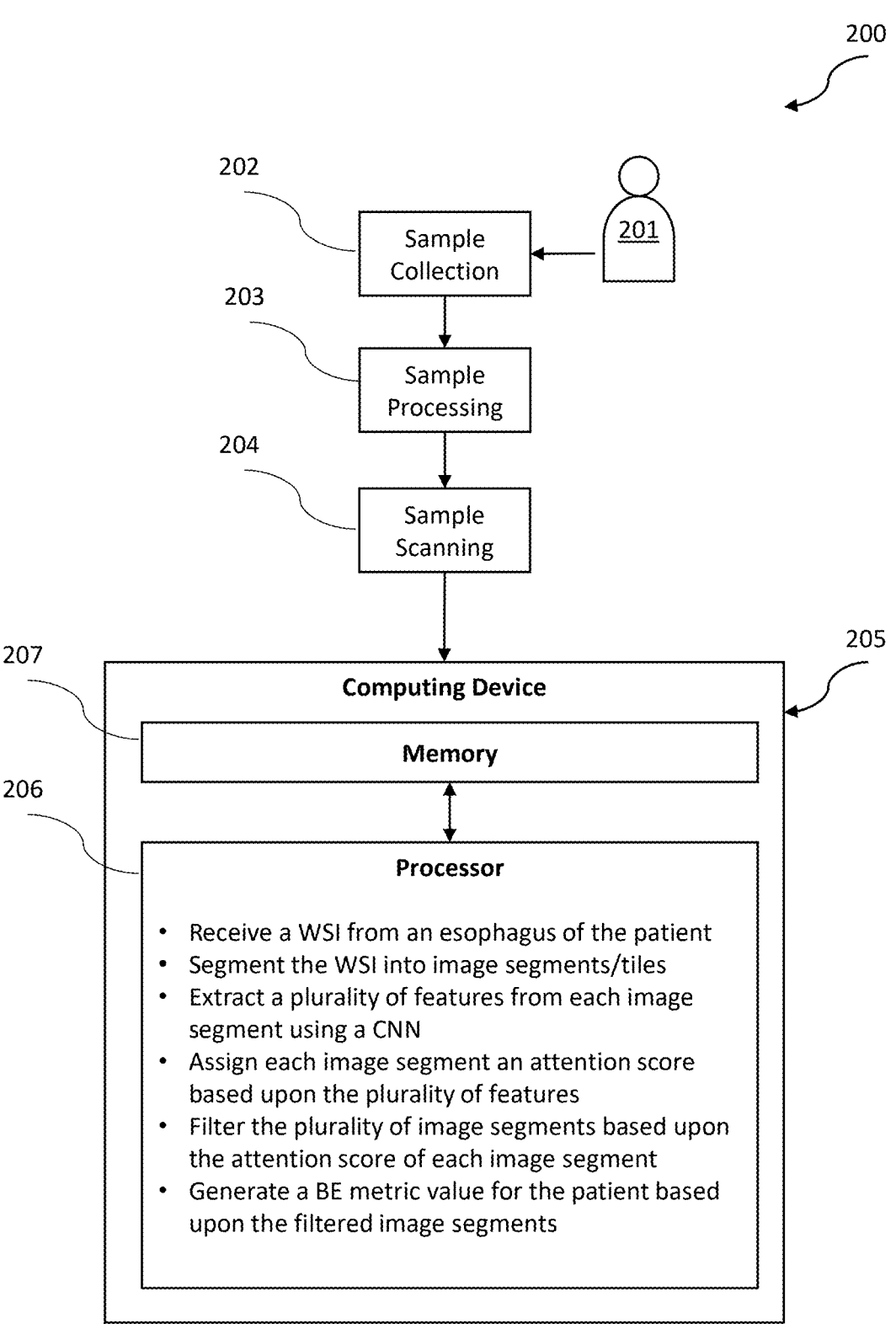
FIG. 10 is a schematic diagram of a system for diagnosing BE, according to a second embodiment of the present disclosure.
Figure 11:
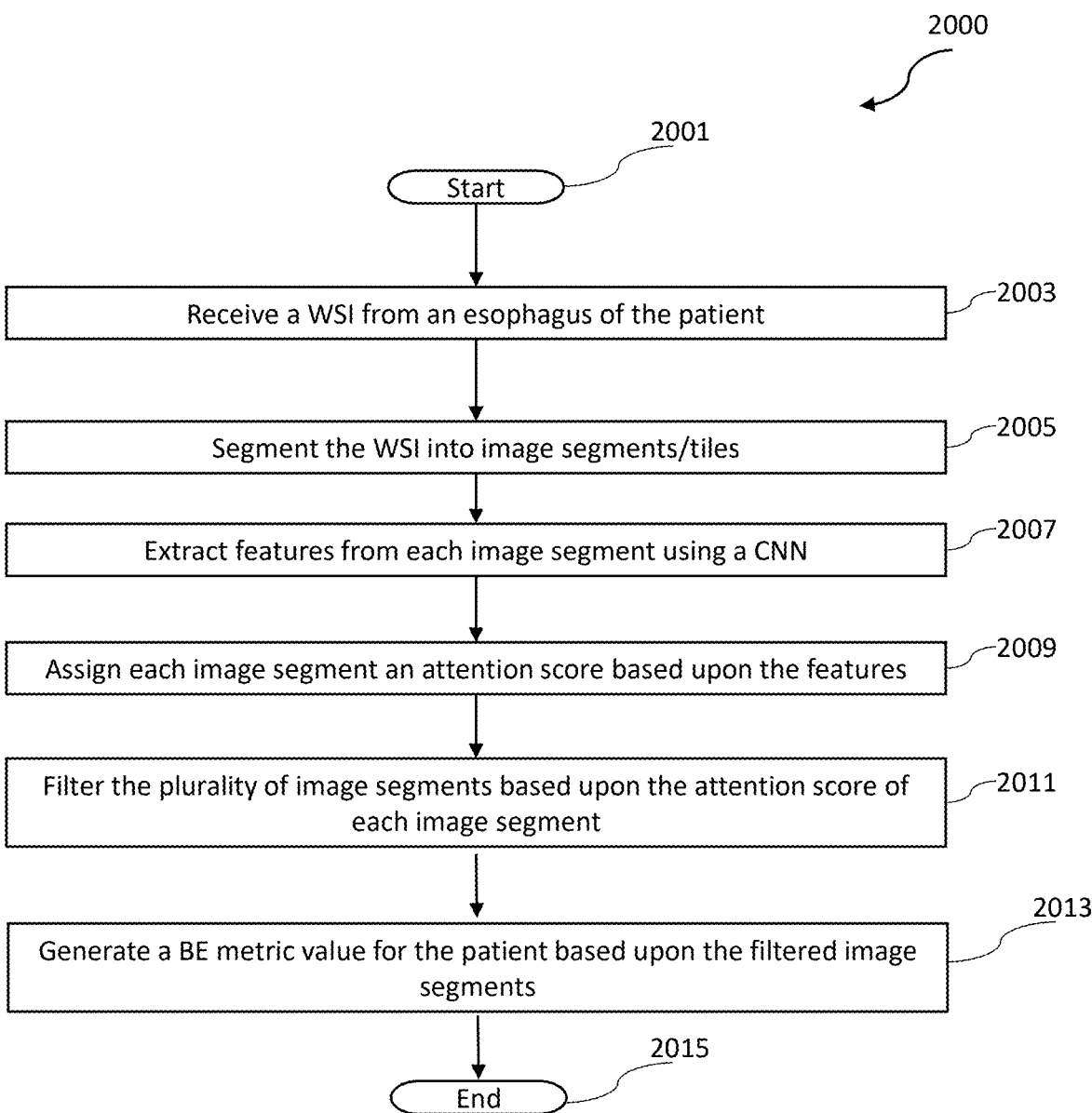
FIG. 11 is a flowchart illustrating a method for diagnosing BE, according to the second embodiment of the present disclosure.

Referring now to FIGS. 10-11, a method for diagnosing BE in a patient 201 is described with reference to a flowchart 2000, which begins at Block 2001. The method comprises receiving a WSI from an esophagus sample from the patient (Block 2003), segmenting the WSI into a plurality of image segments (Block 2005), and extracting a plurality of features from each image segment using a CNN (Block 2007). The method also includes assigning each image segment an attention score based upon the plurality of features (Block 2009), filtering the plurality of image segments based upon the attention score of each image segment (Block 2011), and generating at least one BE metric value for the patient based upon the filtered image segments (Block 2013), the at least one BE metric value indicating a probability that tissue with a propensity to progress to BE exists within the WSI. The method ends at Block 2015.

In some embodiments, the BE progression classifier disclosed herein now makes use of the machine learning model, modified by the teachings herein, disclosed in Lu, M. Y., Williamson, D. F., Chen, T. Y., Chen, R. J., Barbieri, M., & Mahmood, F. (2021); "Data-efficient and weakly supervised computational pathology on whole-slide images"; Nature biomedical engineering, 5(6), 555-570, the entire contents of which are hereby incorporated by reference.

In the first embodiment of the system 100, the classifier was a CNN, such as EfficientNet, which classified each individual image tile (fraction of a whole slide image) as BEN or BEP. In the second embodiment of the system 200, the model makes use of a CNN to extract features from each image tile within a whole slide image. The collection of extracted features is sent to the attention network, which ultimately produces attention scores for each tile in order to summarize them based on the attention values. Additionally, a clustering network for each class learns to cluster tiles with high and low attention values to filter out tiles with attention values between these groups. The constrained, extracted feature values are then used for classifying if the tissue on the slide has propensity to progress or not.

Helpfully, the architecture of the second embodiment of the system 200 was chosen so that when creating training datasets or when using the product in a clinical setting a ROI does not have to be chosen. Part of the Clustering-constrained Attention Multiple instance learning (CLAM) pipeline described in Lu et al. "Data-efficient and weakly supervised computational pathology on whole-slide images" automatically filters out tiles without tissue using pixel value thresholding and the rest of the tiles are able to be used as a collection so the model can learn to filter out irrelevant tissue tiles, thereby eliminating the need for annotations to filter out irrelevant tissue portions. The attention network provides direct visualization of what inputs the model is paying attention to during training, which can provide increased interpretability. Predicting with a collection of tiles allows the model to make use of the small isolated area for the prediction rather than overfitting to the overabundance of other features within the image.

In particular, the CLAM pipeline is now described. The CLAM pipeline is a deep-learning-based weakly-supervised method that uses attention-based learning to automatically identify sub-regions of high diagnostic value to accurately classify the WSI, while also utilizing instance-level clustering over the representative regions identified to constrain and refine the feature space.

Figure 13:
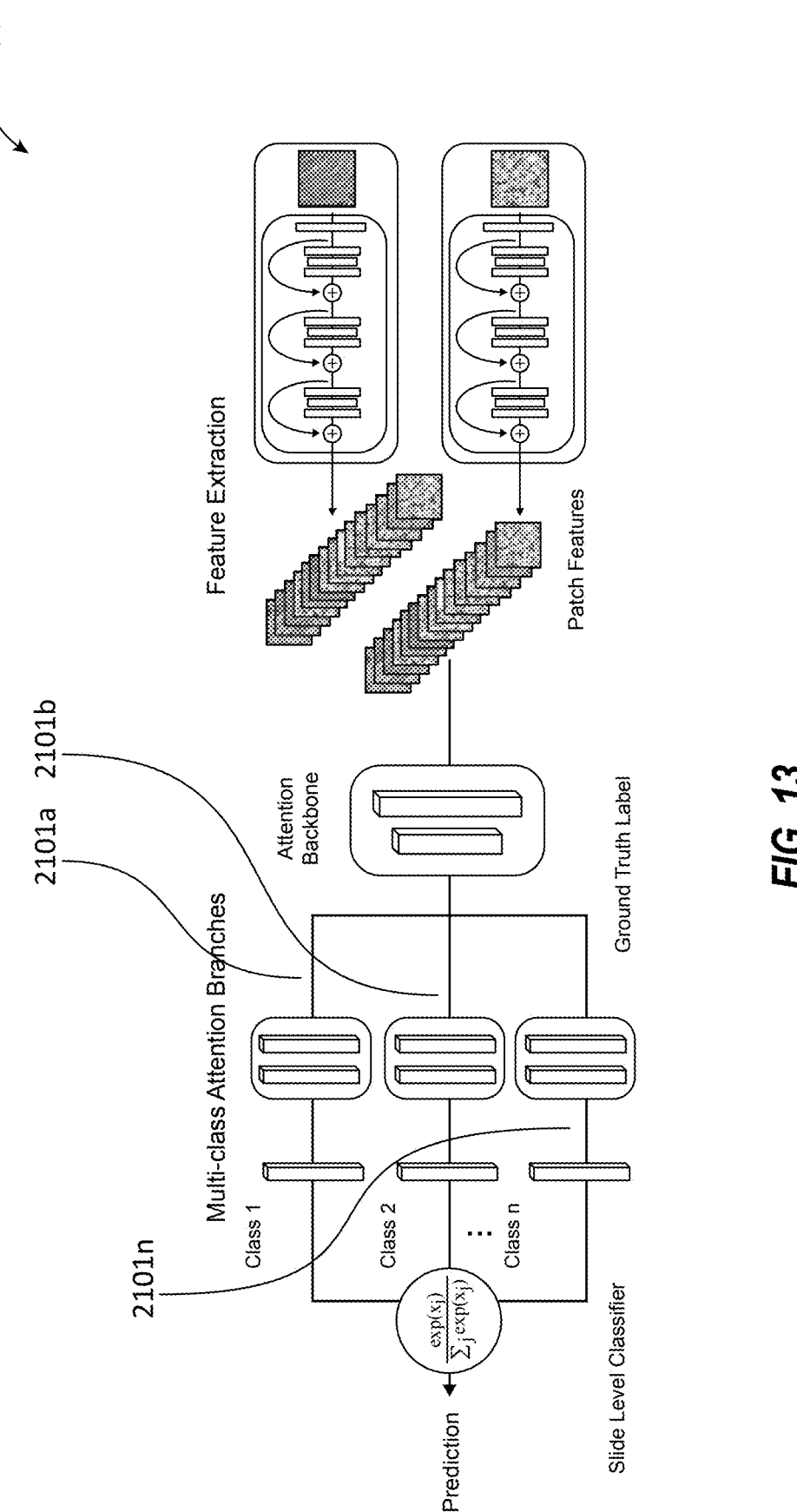
FIG. 13 is a diagram of an exemplary embodiment of an attention network in the system of FIG. 10.
Figure 14:
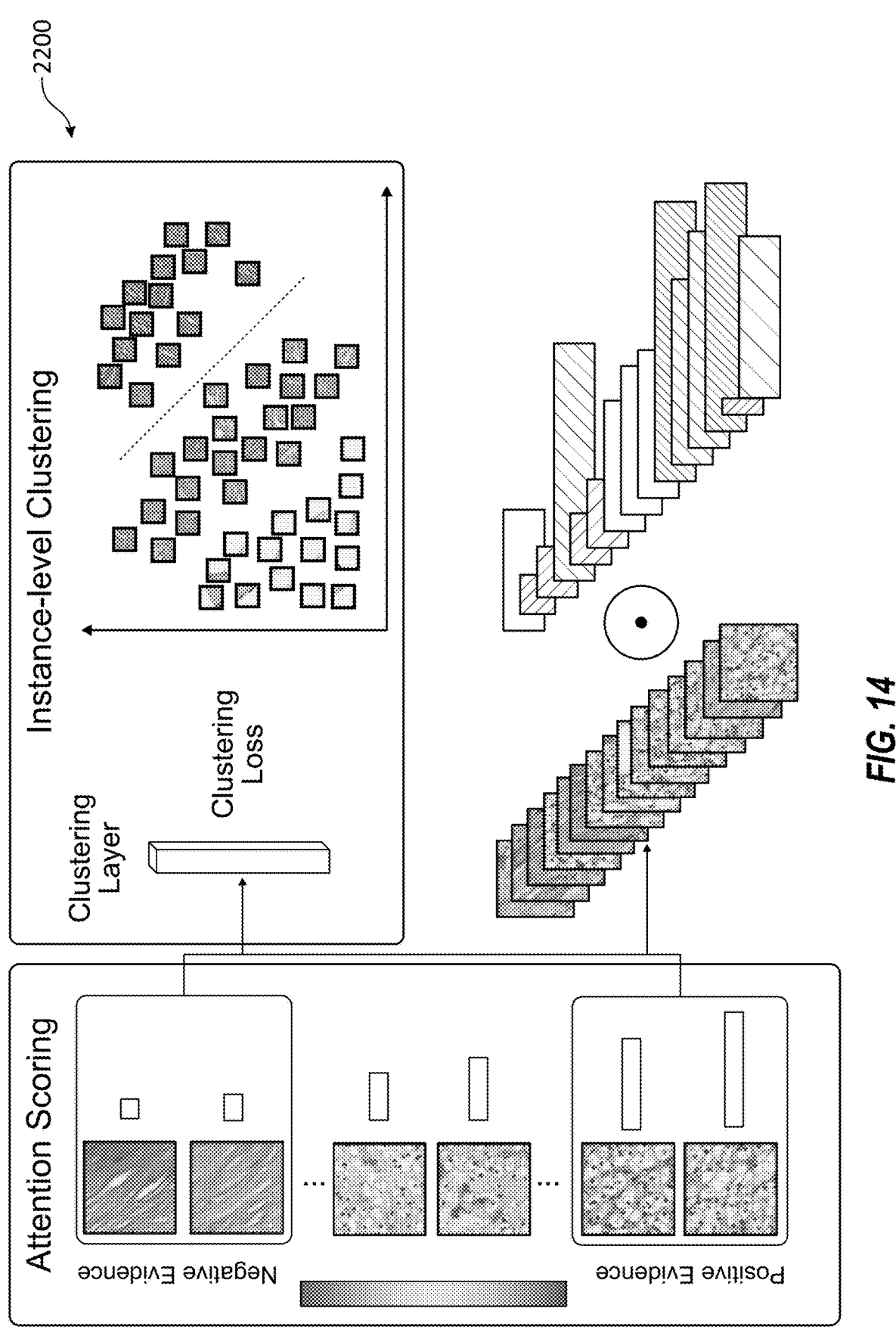
FIG. 14 is a diagram of an exemplary embodiment of a cluster network in the system of FIG. 10.

For whole slide-level learning without annotation, the CLAM pipeline uses an attention-based pooling function for aggregating patch-level features into slide-level representations for classification. At a high level, during both training and inference, the model examines and ranks all patches within the tissue regions of a WSI, assigning an attention score for each patch, which informs its contribution or importance to the collective, slide-level representation for a specific class (FIG. 13). This interpretation of the attention score is reflected in the slide-level aggregation rule of attention-based pooling, which computes the slide-level representation as the average of all patches in the slide weighted by their respective attention score.

Figure 12:
FIG. 12 is a diagram of an exemplary embodiment of WSI segmentation in the system of FIG. 10.
Figure 12:
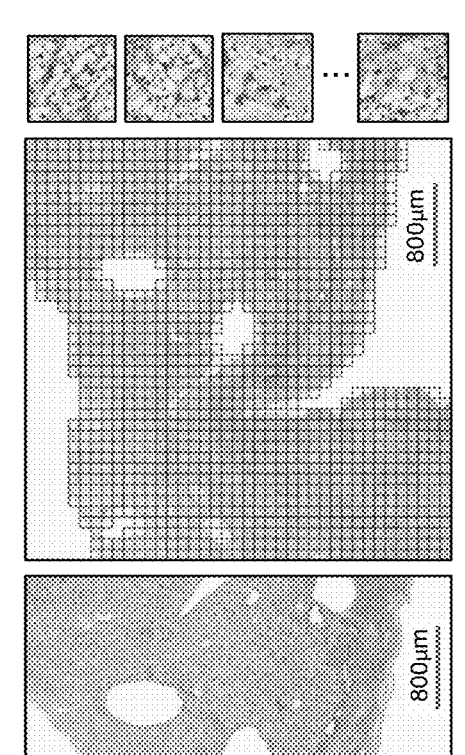

Unlike the standard multiple instance learning algorithm, which was designed specifically for weakly-supervised positive/negative binary classification (e.g., cancer vs. normal), the CLAM pipeline is designed to solve generic multi-class classification problems. The CLAM pipeline has n parallel attention branches that together calculate n unique slide-level representations, where each representation is determined from a different set of highly-attended regions in the image viewed by the network as strong positive evidence for the one of n classes in a multi-class diagnostic task (FIGS. 12-13). Each class-specific slide representation is then examined by a classification layer to obtain the final probability score predictions for the whole slide.

Under the MIL formulation and the weakly-supervised learning paradigm in general, one major bottleneck in developing high-performance machine learning classifiers for computational pathology is the inefficient usage of labeled WSI data. For example, when only the slide-level labels are known, despite having access to many (up to hundreds of thousands) instances or patches, the standard multiple learning algorithm uses maximum pooling and thus uses the gradient signal from only a single instance in each slide to update the learning parameters of the neural network model. This drawback can be used to partly explain why empirically, a deep learning model trained using MIL would require observing an enormous number of example WSIs annotated at the slide level to achieve high performance even for simple tasks such as binary classification.

To address the data inefficiency in existing weakly-supervised learning algorithms for computational pathology, the CLAM pipeline adopts the attention-based pooling aggregation rule instead of max pooling. Additionally, the CLAM pipeline uses of the slide-level ground truth label and the attention scores predicted by the network to generate pseudo-labels for both highly attended and weakly attended patches as a novel means to increase the supervisory signals for learning a rich, separable, patch-level feature space.

During training, the network learns from an additional supervised learning task of clustering the most and least attended patches of each class into distinct clusters. Additionally, it is possible to incorporate domain knowledge into the instance level clustering to add further supervision. Following the mutual exclusivity assumption, in addition to supervising the attention branch for which the ground truth class is present, the CLAM pipeline supervises the attention network branches corresponding to the remaining classes by clustering their highly attended instances as "false positive" evidence for their respective classes.

In order to make the CLAM pipeline a high-throughput pipeline without requiring dedicated, high performance compute clusters, the CLAM pipeline uses a WSI processing toolbox. The CLAM pipeline first automatically segments the tissue region of each slide and divides it into many smaller patches (e.g., 256×256 pixels) so they can serve as direct inputs to a CNN. Next, using a pretrained CNN for feature extraction, the CLAM converts all tissue patches into sets of low-dimensional feature embeddings (FIG. 13). Following this feature extraction, both training and inference can occur in the low-dimensional feature space instead of the high-dimensional pixel space.

The volume of the data space is decreased nearly 200-fold, and the CLAM pipeline can drastically reduce the subsequent computation required to train supervised deep learning models. In practice, working with a low-dimensional feature space enables training models on thousands of gigapixel-sized resection slides within hours on modern consumer-grade workstations.

It should be appreciated that one or more of the features from the system 100 may be combined with the system 200, and vice versa.

Many modifications and other embodiments of the present disclosure will come to the mind of one skilled in the art having the benefit of the teachings presented in the foregoing descriptions and the associated drawings. Therefore, it is understood that the present disclosure is not to be limited to the specific embodiments disclosed, and that modifications and embodiments are intended to be included within the scope of the appended claims.

The invention claimed is:

1. A system for diagnosing Barrett's esophagus (BE) in a patient, the system comprising:
   a processor and memory coupled thereto, the processor configured to
   receive a whole slide image (WSI) from an esophagus sample from the patient,
   segment the WSI into a plurality of image segments,
   extract a plurality of features from each image segment using a convolutional neural network (CNN),
   assign each image segment an attention score based upon the plurality of features,
   filter the plurality of image segments based upon the attention score of each image segment, the filtering comprising
      clustering the plurality of image segments based upon respective attention scores and upper and lower thresholds, and
      removing a portion of the image segments with attention scores between the upper and lower thresholds,
   generate at least one BE metric value for the patient based upon the filtered image segments, the at least one BE metric value indicating a probability that tissue with a propensity to progress to BE exists within the WSI.

2. The system of claim 1 wherein the assigning comprises ingesting the plurality of features for each image segment into an attention network.

3. The system of claim 1 wherein the assigning comprises generating a plurality of branches, each branch associated with a respective class.

4. The system of claim 3 wherein at least one branch is associated with a slide-level ground truth label class.

5. The system of claim 1 wherein the filtering comprises ingesting the plurality of features for each image segment into a cluster network.

6. The system of claim 1 wherein the filtering comprises removing image segments having less than a threshold amount of tissue.

7. The system of claim 1 wherein the at least one BE metric value comprises a plurality thereof, the plurality of BE metric values comprising a first BE metric indicating a probability that tissue with a propensity to progress to BE exists within the WSI.

8. The system of claim 1 wherein the processor is configured to directly ingest the plurality of image segments into the CNN.

9. The system of claim 1 wherein the extracting comprises placing the plurality of features from each image segment in a data space less than a data space of the WSI.

10. A system for diagnosing Barrett's esophagus (BE) in a patient, the system comprising:
    a processor and memory coupled thereto, the processor configured to
    receive a whole slide image (WSI) from an esophagus sample from the patient,
    segment the WSI into a plurality of image segments,
    directly ingest the plurality of image segments into a convolutional neural network (CNN),
    extract a plurality of features from each image segment using the CNN,
    assign each image segment an attention score based upon the plurality of features,
    filter the plurality of image segments based upon the attention score of each image segment, the filtering comprising
       ingesting the plurality of features for each image segment into a cluster network,
       clustering the plurality of image segments with attention scores based upon respective attention scores and upper and lower thresholds, and
       removing a portion of the image segments with attention scores between the first and second thresholds, and
    generate at least one BE metric value for the patient based upon the filtered image segments, the at least one BE metric value indicating a probability that tissue with a propensity to progress to BE exists within the WSI.

11. The system of claim 10 wherein the assigning comprises ingesting the plurality of features for each image segment into an attention network.

12. The system of claim 10 wherein the assigning comprises generating a plurality of branches, each branch associated with a respective class.

13. The system of claim 12 wherein at least one branch is associated with a slide-level ground truth label class.

14. The system of claim 10 wherein the filtering comprises removing image segments having less than a threshold amount of tissue.

15. The system of claim 10 wherein the at least one BE metric value comprises a plurality thereof, the plurality of BE metric values comprising a first BE metric indicating a probability that tissue with a propensity to progress to BE exists within the WSI.

16. The system of claim 10 wherein the extracting comprises placing the plurality of features from each image segment in a data space less than a data space of the WSI.

17. A method for diagnosing Barrett's esophagus (BE) in a patient, the method comprising:

receiving a whole slide image (WSI) from an esophagus sample from the patient;

segmenting the WSI into a plurality of image segments;

extracting a plurality of features from each image segment using a convolutional neural network (CNN);

assigning each image segment an attention score based upon the plurality of features;

filtering the plurality of image segments based upon the attention score of each image segment, the filtering comprising clustering the plurality of image segments based upon respective attention scores and upper and lower thresholds, and removing a portion of the image segments with attention scores between the upper and lower thresholds; and generating at least one BE metric value for the patient based upon the filtered image segments, the at least one BE metric value indicating a probability that tissue with a propensity to progress to BE exists within the WSI.

18. The method of claim 17 wherein the assigning comprises ingesting the plurality of features for each image segment into an attention network.

19. The method of claim 17 wherein the assigning comprises generating a plurality of branches, each branch associated with a respective class.

20. The method of claim 19 wherein at least one branch is associated with a slide-level ground truth label class.

* * * * *